(12) United States Patent
Li et al.

(10) Patent No.: US 8,798,229 B2
(45) Date of Patent: Aug. 5, 2014

(54) DETECTOR MODULES AND METHODS OF MANUFACTURING

(75) Inventors: Wen Li, Clifton Park, NY (US); Naresh Kesavan Rao, Clifton Park, NY (US); Abdelaziz Ikhlef, Hartland, WI (US); Jeffrey Kautzer, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 384 days.

(21) Appl. No.: 13/250,945

(22) Filed: Sep. 30, 2011

(65) Prior Publication Data
US 2013/0083887 A1 Apr. 4, 2013

(51) Int. Cl.
*A61B 6/03* (2006.01)
*H05G 1/64* (2006.01)

(52) U.S. Cl.
USPC ... 378/19; 378/98.8; 250/370.09; 250/370.14

(58) Field of Classification Search
USPC ............... 378/19, 98.8; 250/370.08, 370.09; 250/370.1, 370.14; 257/444–448, 458
See application file for complete search history.

(56) References Cited

U.S. PATENT DOCUMENTS

| | | | | |
|---|---|---|---|---|
| 6,393,092 B1 * | 5/2002 | Yoshida | ........................... | 378/19 |
| 6,426,991 B1 * | 7/2002 | Mattson et al. | ................. | 378/19 |
| 6,510,195 B1 * | 1/2003 | Chappo et al. | ................. | 378/19 |
| 6,512,809 B2 * | 1/2003 | Doubrava et al. | ............... | 378/19 |
| 6,658,082 B2 * | 12/2003 | Okumura et al. | ............... | 378/19 |
| 6,671,347 B2 * | 12/2003 | Tashiro et al. | ............... | 378/98.8 |
| 6,891,242 B2 | 5/2005 | Gidon et al. | | |
| 6,906,332 B2 * | 6/2005 | Tashiro et al. | ........... | 250/370.11 |
| 7,136,452 B2 * | 11/2006 | Spartiotis et al. | ............... | 378/19 |
| 7,161,155 B1 * | 1/2007 | Deych | ........................ | 250/370.11 |
| 7,230,247 B2 * | 6/2007 | Shibayama | ............... | 250/370.11 |
| 7,566,876 B2 * | 7/2009 | Moody et al. | ........... | 250/370.08 |
| 7,652,257 B2 * | 1/2010 | Li et al. | .................... | 250/370.01 |
| 7,655,494 B2 | 2/2010 | Rhodes | | |
| 7,795,650 B2 | 9/2010 | Eminoglu et al. | | |
| 7,872,237 B2 * | 1/2011 | Puhakka et al. | ......... | 250/370.08 |
| 7,948,017 B2 | 5/2011 | Tredwell et al. | | |
| 8,022,369 B2 * | 9/2011 | Orava et al. | ............. | 250/370.05 |
| 8,237,126 B2 * | 8/2012 | Von Kanel et al. | ...... | 250/370.09 |
| 8,288,733 B2 * | 10/2012 | Herrmann et al. | ....... | 250/370.09 |
| 8,461,541 B2 * | 6/2013 | Garcia et al. | ............. | 250/370.01 |
| 2010/0074396 A1 | 3/2010 | Schmand et al. | | |
| 2010/0102242 A1 | 4/2010 | Burr et al. | | |
| 2011/0019055 A1 | 1/2011 | Jaworski et al. | | |
| 2011/0024774 A1 | 2/2011 | Tredwell et al. | | |

OTHER PUBLICATIONS

Steadman et al., "A CMOS Photodiode Array with In-Pixel Data Acquisition System", IEEE Journal of Solid-State Circuits, vol. 39, Issue 7, pp. 1034-1043, Jul. 2004.

\* cited by examiner

*Primary Examiner* — Allen C. Ho
(74) *Attorney, Agent, or Firm* — The Small Patent Law Group; Dean D. Small

(57) ABSTRACT

Detector modules and methods of manufacturing are provided. One detector module includes a detector having a silicon wafer structure formed from a first layer having a first resistivity and a second layer having a second resistivity, wherein the first resistivity is greater than the second resistivity. The detector further includes a photosensor device provided with the first layer on a first side of the silicon wafer and one or more readout electronics provided with the second layer on a second side of the silicon wafer, with the first side being a different side than the second side.

20 Claims, 5 Drawing Sheets

US 8,798,229 B2

DETECTOR MODULES AND METHODS OF MANUFACTURING

BACKGROUND

Imaging systems are widely used to capture images of objects. For example, diagnostic images of a person or an animal may be obtained to assist a doctor or other health care professional in making an accurate diagnosis. Another example includes imaging luggage, shipping containers, and/or the like for security and/or industrial inspection applications. Imaging systems often include an energy source and one or more detectors. In particular, energy, for example x-rays, produced by the source travel through the object being imaged and are detected by the detectors. In response thereto, the detectors produce digital signals that represent the sensed energy used for subsequent processing and image reconstruction.

Some imaging systems, such as some computed tomography (CT) imaging systems, continue to increase the number of imaging pixels and the detector coverage. Accordingly, the number of analog interconnections between detector pixel arrays and the readout electronics increases, which increases the complexity of the packaging design to integrate the photosensor array and readout electronics including the A/D converter. For example, some package designs include complex ceramic substrates that are expensive to manufacture. These ceramics also have increased risk in interconnection yields and reliability. Some other package designs include the integration of photosensor array and readout electronics on the same side of a silicon wafer. However, this design results in the loss of the active detection area of the photosensor array and compromises performance as a result of the different requirements on wafer properties for the photosensor and readout electronics.

BRIEF DESCRIPTION

In one embodiment, a detector is provided that includes a silicon wafer structure formed from a first layer having a first resistivity and a second layer having a second resistivity, wherein the first resistivity is greater than the second resistivity. The detector further includes a photosensor device provided with the first layer on a first side of the silicon wafer and one or more readout electronics provided with the second layer on a second side of the silicon wafer, with the first side being a different side than the second side.

In another embodiment, an imaging system is provided that includes an x-ray source for generating x-rays and a detector for detecting x-rays generated by the x-ray source after passing through an object. The detector includes a plurality of modules, each module includes detector elements formed from (i) a silicon wafer structure having a first layer with a first resistivity and a second layer having a second resistivity, wherein the first resistivity is greater than the second resistivity, (ii) a photosensor device provided with the first layer on a first side of the silicon wafer and (iii) one or more readout electronics provided with the second layer on a second side of the silicon wafer, the first side being a different side than the second side, wherein digital signals are output from the one or more readout electronics. The imaging system further includes a processor for reconstructing an image of the object using the digital signals.

In yet another embodiment, a method for forming a detector module is provided that includes fabricating a photosensor array on a first side of a silicon wafer, wherein the silicon wafer comprises a plurality of layers each having a different resistivity. The method also includes fabricating readout electronics on a second side of the silicon wafer opposite the first side and forming a conductive via through the silicon wafer interconnecting the photosensor array and the readout electronics.

DETAILED DESCRIPTION

Figure 1:
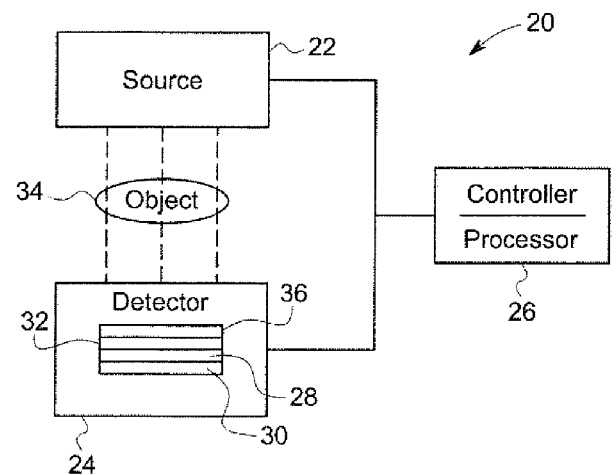
FIG. 1 is a simplified schematic block diagram of an exemplary embodiment of an imaging system.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the term "reconstructing" or "rendering" an image or data set is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image. In an exemplary embodiment, the "object" being imaged is a human individual. However, the object may alternatively be of another living creature besides a human individual. Moreover, the object is not limited to living creatures, but rather may be of inanimate objects, such as, but not limited to, luggage, shipping containers, and/or the like.

Various embodiments provide photosensor arrays and readout electronic circuits for detector modules (e.g., imaging detector modules) that are fabricated and provided on different sides of a silicon structure. By practicing various embodiments, the active detection area of the detector modules is increased and the number of interconnections in chip level packaging is reduced. Additionally, by practicing various embodiments, thermal management requirements may be reduced and fill-factor restrictions reduced or eliminated. Also, by practicing various embodiments, and in imaging applications, a finer pitch detector may be provided.

The various embodiments may be implemented within imaging systems, which are described herein in connection with computed tomography (CT) systems. However, the various embodiments may be implemented in connection with different types of imaging systems, such as positron emission tomography (PET) systems and nuclear medicine systems, such as single-photon emission computed tomography (SPECT) systems, as well as other types of imaging systems. Applications of imaging systems include medical applications, security applications, industrial inspection applications, and/or the like. Thus, although embodiments are described and illustrated herein with respect to a CT imaging system having detectors that detect x-rays, the various embodiments may be used with any other imaging modalities and may be used to detect any other type of electromagnetic energy. Moreover, the various embodiments described and/or illustrated herein are applicable with single slice and/or multi-slice configured systems.

Referring now to FIG. 1, an imaging system 20 includes a source 22 of electromagnetic energy, one or more detectors 24, and a controller/processor 26. The one or more detectors 24 also include a photosensor array 28 and readout electronics 30 (e.g., an analog-to-digital (A/D) converter to convert an analog signal current into a digital signal, or a combination of an amplifier and an A/D converter with the amplifier to convert an analog signal current into an analog voltage signal and the A/D converter to convert the voltage signal into a digital signal). The photosensor array 28 and readout electronics 30 in various embodiments are formed on two sides of the same silicon wafer with interconnections provided with conductive vias as described in more detail herein. A post-object collimator 36 (e.g., a post-patient collimator) and a scintillator 32 is also provided as described in more detail below.

The controller/processor 26 may provide power and/or timing control signals to the source 22. The detector 24 senses energy emitted by the source 22 that has passed through an object 34 being imaged and the post-object collimator 36. In response thereto, the scintillator 32 converts the X-rays received into optical photons, and the photosensor array 28 converts the optical photons into electrical current signals that represent the sensed energy. The readout electronics 30, such as A/D converters, sample the analog current signals received from the photosensor array 28 and converts the data to digital signals. The controller/processor 26 performs subsequent processing and image reconstruction using the received digital signals. The reconstructed image may be stored and/or displayed by the controller/processor 26 and/or another device.

In various embodiments, the detector 24 is an indirect conversion detector wherein the scintillator 32 converts electromagnetic energy into visible (or near-UV) light photons, which are then converted to electrical analog signals by the photosensor array 28. The detector 24 may be any type of indirect conversion detector, such as, but not limited to, any detector with high density rare-earth ceramic scintillators.

Figure 2:
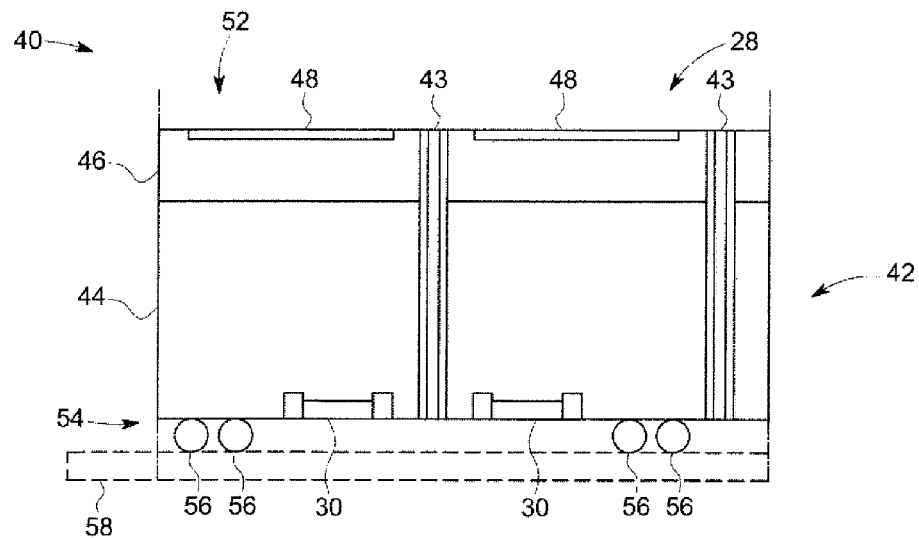
FIG. 2 is a simplified cross-sectional view of an integrated photosensor array and readout electronics arrangement in accordance with an embodiment.

As shown in FIG. 2, an integrated photosensor array and readout electronics arrangement 40 may be provided that includes the photosensor array 28 on one side of a silicon wafer 42 and the readout electronics 30 on a different side of the silicon wafer 42 with interconnections provided by conductive through conductive vias 43 (e.g., vias with heavily doped poly-Si refills). Using the integrated photosensor array and readout electronics arrangement 40, in various embodiments, a fully two-dimensional (2D) tileable silicon chip for a CT detector module may be provided. In various embodiments, the silicon wafer 42 is an epi-wafer, which may be any wafer of semiconducting material formed by epitaxial growth (also referred to as epitaxy). The epi-wafer may be formed from any suitable method such as growing the epitaxial layer on existing silicon substrate or direct silicon-to-silicon bonding. The epi-wafer may be formed from different materials, such as semiconductor materials including gallium nitride (GaN), with different dopants such as gallium, indium, aluminum, nitrogen, phosphorus or arsenic, or combinations thereof, among others.

In one embodiment, the silicon wafer 42 is a multilayer wafer that includes a substrate 44 with a high resistivity layer 46 (e.g., greater than 800 ohm-cm). For example, the high resistivity layer 46 may have a resistivity suitable for fabrication of a photodiode, such as a zero bias PIN diode as described herein. In this embodiment, the silicon wafer 42 may be formed from two layers of silicon material. For example, the substrate 44 may be formed from an X—Si substrate material having a resistivity suitable for fabricating complementary metal-oxide-semiconductor (CMOS) mixed signal readout electronics. The high resistivity layer 46 may be formed as a high resistivity epi-layer. In various embodiments, the multi-layer structure may be formed from process steps that include oxidation, diffusion or ion implantation, photolithography and metallization. For example, in one embodiment, an N-type substrate may be provided with a P-type boron implant to form a pixelated pattern of photodiode array, which defines a radiation detecting face, such as of a CT detector. In one embodiment, diodes 48, which may be configured as pixelated photodiodes are formed by the boron implants. However, it should be noted that different processes may be used instead of ion implantation, such as diffusion with a gas diffusion source. It should be noted that inter-pixel electrical isolation structure may be provided, for example, using a suitable diffusion or trench/etching process to isolate adjacent diodes 48 from each other as described in more detail herein. The diodes 48 operate at a zero bias in various embodiments, which reduces or minimizes the dark leakage current sent to the readout electronics 30. For example, the diodes 48 may be photodiodes that detect light generated from the scintillator 32 (shown in FIG. 1) that is generated based on x-rays or gamma rays impinging on the scintillator 32. The light is converted to electrical current signals by the diodes 48, such as for use in CT imaging.

It should be noted that any suitable CMOS fabrication technique may be used in fabricating some embodiments. The various layers also may be formed from any suitable process, such as epitaxial growth as described above or silicon to silicon direct bonding, among others. The process used to form the layers may be based on, for example, the device requirements or the thickness of the layers.

In one embodiment, the substrate 44 is a medium resistivity layer having a resistivity less than the high resistivity layer 46. For example, in one embodiment, the high resistivity layer 46 has a resistance of greater than about 800 ohm-cm and the substrate 44 has a resistivity of between about 10 ohm-cm and 100 ohm-cm. However, other resistivity values may be provided as desired or needed. In various embodiments, the medium resistivity is a resistivity suitable for fabricating readout electronics, such as the readout electronics 30. In various embodiments, the substrate 44 decouples the resistivity requirements for the diodes 48 and the readout electronics 30.

In one embodiment, the diodes 48 correspond to detector pixels and a conductive via 43 is provided per pixel as shown. Thus, the diodes 48 in this embodiment form the photosensor array 28 (shown in FIG. 1). The conductive vias 43 provide electrical connection between the diodes 48 on one side 52 of the silicon wafer 42 (shown as a top side) and the readout electronics 30 on an opposite side 54 of the silicon wafer 42 (shown as the bottom side). In various embodiments, the readout electronics 30 are provided in a 1:1 or about 1:1 correlation with the pixelated pattern of diodes 48. The readout electronics 30 may be, for example, an A/D converter implanted or embedded on an opposite side 54 of the wafer 42 to the diodes 48.

Additionally, data or control interconnect bonds 56 (e.g., epoxy or solder) are provided on the opposite side 54, which are digital signal interconnects in this embodiment. The interconnect bonds 56 may be formed from any suitable material, such as metal, solder (e.g., solder bumps or balls) or conductive adhesive (e.g., epoxy plus a filler, such as nickel or graphite), among others. The interconnect bonds 56 provide, for example, digital communication and power transmission.

It should be noted that the scintillator 32 (shown in FIG. 1) is provided on the top side 52 of the high resistivity layer 46 as viewed in FIG. 2. Additionally, the interconnect bonds 56 may connect to, for example, planar circuitry or a printed circuit board (PCB) 58 on the bottom side 54 of the substrate 42 as viewed in FIG. 2.

In various embodiments, the diodes 48, which may be configured as photosensors, and the readout electronics 30 are fabricated on different and individual sides of an epi-wafer and electrically connected with the conductive vias 43. Thus, a double-sided photolithography process may be used in some embodiments. The channel layout for the readout electronics 30 is generally in a pixelated pattern complementary to the arrangement of the diodes 48, which may be arranged in a two-dimensional array. However, it should be noted that the channel pitch for the readout electronics 30 may be smaller than the pitch of the array for the diodes 48, which provides spacing, such as to include passive components (e.g., power line filtering components).

It should be noted that the diodes 48 and the readout electronics 30 may be formed using any suitable process. For example, any suitable doping and masking process may be used to form components within the structure. Additionally, any suitable depositing process with masking and/or etching with metal sputtering may be provided to provide components on any layer.

Figure 3:
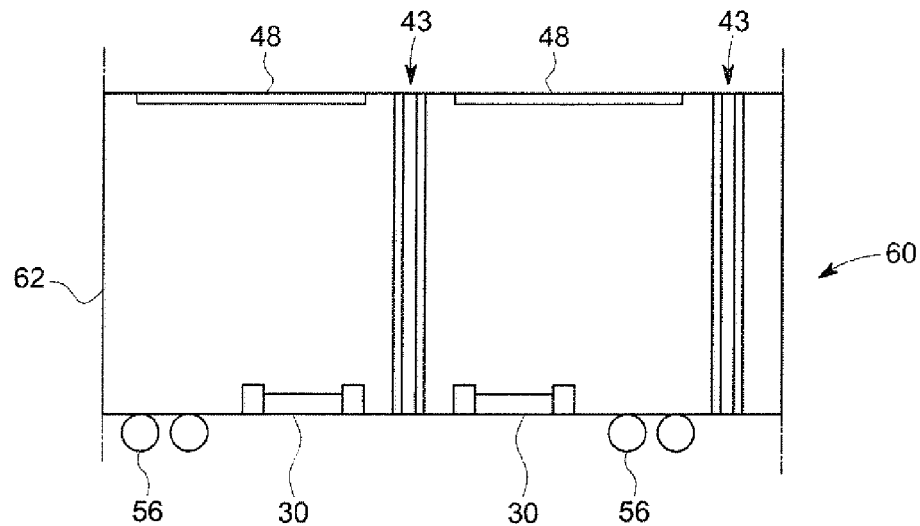
FIG. 3 is a simplified cross-sectional view of an integrated photosensor array and readout electronics arrangement in accordance with another embodiment.

The integration of the components, in particular, the diodes 48 and the readout electronics 30 in a wafer design may be provided in different configurations or arrangements. For example, in another embodiment, as shown in FIG. 3, an integrated photosensor array and readout electronics arrangement 60 is provided that has a single layer configuration. It should be noted that like numerals represent like parts throughout the figures. In this embodiment, a self-supporting single layer silicon structure is provided having a single high resistivity layer 62 that is fabricated to define a device layer for supporting or having the diodes 48 and the readout electronics 30 deposited, implanted or embedded therein or thereon. The thickness of the high resistivity layer 62 may vary, for example, in one embodiment, the high resistivity layer 62 has a thickness of 20-40 microns. However, the thickness of the high resistivity layer 62 may be greater than 40 microns. The high resistivity layer 62 in some embodiments has a resistivity of greater than about 800 ohms-cm. However, the resistivity may be greater or smaller. It should be noted that the high resistivity layer 62 may be provided or formed similar to the high resistivity layer 46 shown in FIG. 2.

Figure 4:
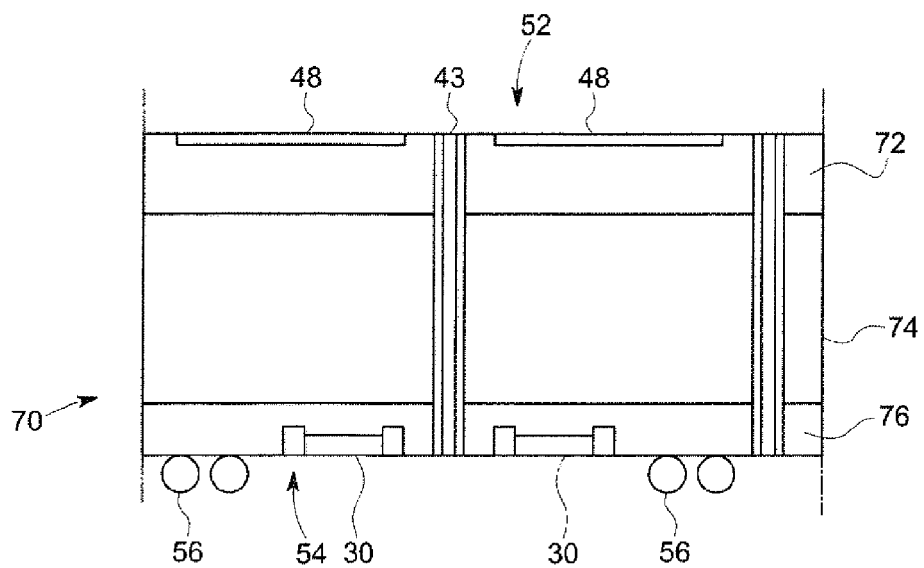
FIG. 4 is a simplified cross-sectional view of an integrated photosensor array and readout electronics arrangement in accordance with another embodiment.

As another example, the diodes 48 and the readout electronics 30 in a wafer design may be provided in a configuration as shown in FIG. 4. In this embodiment, an integrated photosensor array and readout electronics arrangement 70 is provided that includes a three layer silicon configuration. In particular, a low resistivity layer 74 is provided between a high resistivity layer 72 and a medium resistivity layer 76. The high resistivity layer 72 and the medium resistivity layer 76 may have, for example, resistivity similar to or different from the high and medium resistivity of the other embodiments. Additionally, in this embodiment, the medium resistivity layer 76 is provided on the bottom side 54 of the structure. The low resistivity layer 74 in one embodiment has a resistivity of less than about 1 ohm-cm. However, greater or smaller resistivity values may be provided. In various embodiments, the low resistivity layer 74 has a resistivity suitable for a ground layer. In the illustrated embodiment, the high resistivity layer 72 and a medium resistivity layer 76 generally define device layers and the low resistivity layer 74 generally defines an isolation layer, which may be, for example, a heavily doped silicon layer.

In one embodiment, epi-layer deposition on both sides of a silicon substrate wafer is provided to form the diodes 48 and the readout electronics 30. It should be noted that the isolation layer provided by the low resistivity layer 74 allows for the device layers, namely the high resistivity layer 72 and a medium resistivity layer 76, in this embodiment, to be formed from material having, for example, independent critical to quality (CTQ) standards or other requirements.

Figure 5:
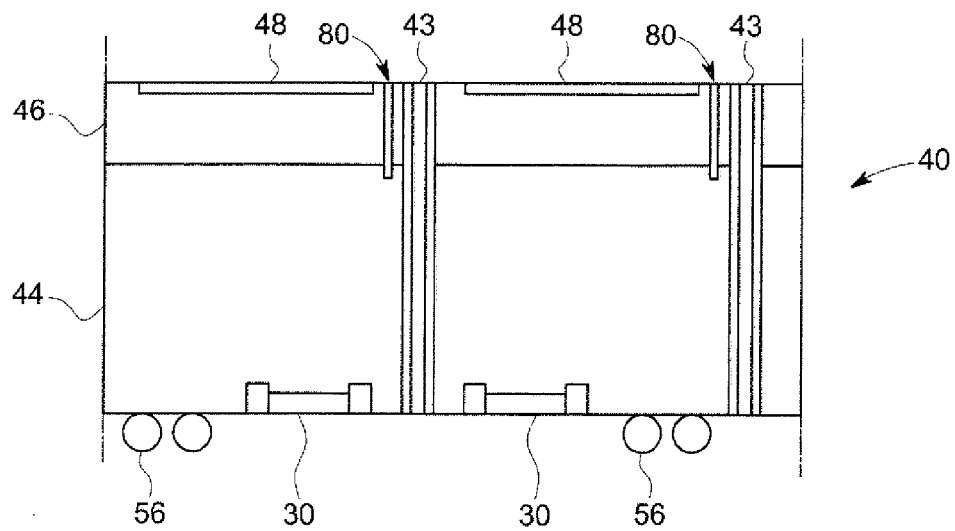
FIG. 5 is a simplified cross-sectional view of the integrated photosensor array and readout electronics arrangement of FIG. 1 showing an isolation structure in accordance with an embodiment.
Figure 6:
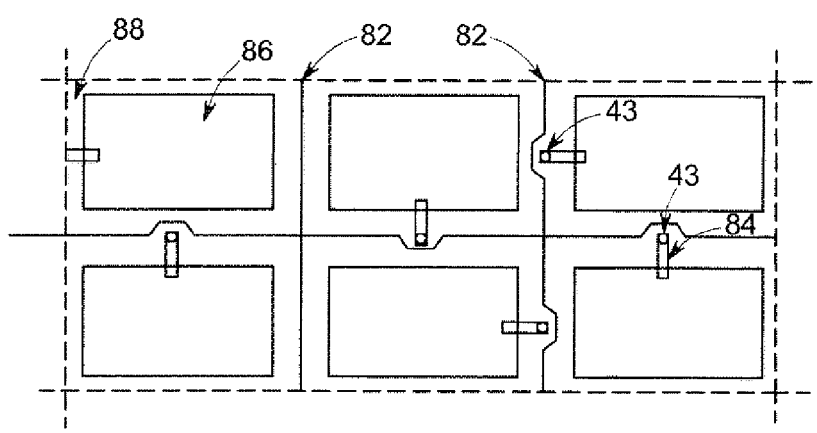
FIG. 6 is a top plan view of the integrated photosensor array and readout electronics arrangement of FIG. 5.

The various portions or components of the various embodiments also may be provided in different configurations and arrangements. For example, the integrated photosensor array and readout electronics arrangement 40 may include inter-pixel isolation structure 80 as shown in FIGS. 5 and 6. In particular, an inter-pixel isolation structure 80 may be provided extending from a surface of the structure through the high resistivity layer 46 (e.g., extending about 20-30 microns therethrough) and into a portion of the substrate 44 (e.g., a few microns into the substrate 44). The inter-pixel isolation structure 80 is generally formed between the diodes 48 and the conductive vias 43. For example, the inter-pixel isolation structure 80 may be formed as a trench using a suitable dry etching process or a suitable deep diffusion process, among others. In one embodiment, a high aspect ratio etch is used to set the width of the trenches 82 for the inter-pixel isolation structure 80. It should be noted that the sidewalls of the trenches 82 may be passivated and the trenches 82 may be refilled with poly-silicon material.

An electrical connector 84 (e.g., an aluminum strip) is provided to electrically connect the conductive via 43 to an active area 86 (e.g., P+doped region), which may be used, for example, to detect optical photons from the scintillator 32 in a CT application. It should be noted that the active areas 86 are surrounded by an intrinsic layer 88.

The inter-pixel isolation structure 80 in various embodiments defines a two-dimensional isolation structure that defines pixels (in this embodiment formed from the active areas 86). The inter-pixel isolation structure 80 may be formed from an etched trench grid as shown in FIG. 6, or may be formed by a diffusion grid with the diffusion in the same doping type as the high resistivity layer 46 (e.g., device layer) and being deep enough to reach the substrate 44.

In one embodiment, the inter-pixel isolation structure 80 may provide isolation allowing for crosstalk improvement to achieve a required or desired spatial resolution for medical CT imaging applications. For example, the inter-pixel isolation structure 80 may provide a desired or required spatial resolution that is independent of the size of the active area 86.

Figure 7:
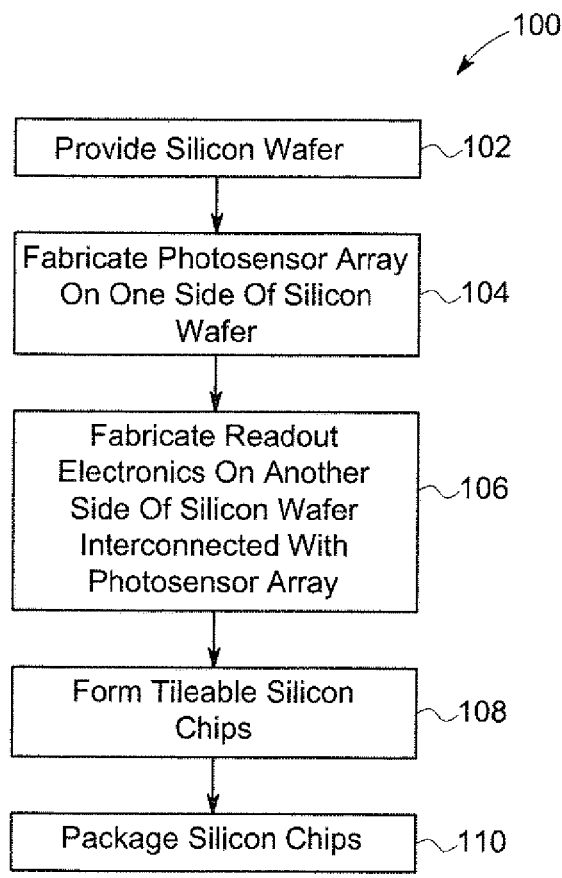
FIG. 7 is a flowchart of method for forming a detector module in accordance with various embodiments having an integrated photosensor array and readout electronics.

Various embodiments provide a method 100 as shown in FIG. 7 for forming a detector module having an integrated photosensor array and readout electronics. In particular, the method 100 includes providing a silicon wafer 42 with a pre-fabricated conductive through-silicon-via array 43 at 102 and fabricating a photosensor array 28 on one side 52 of the silicon wafer at 104. At 106, readout electronics 30 are fabricated on the other side 54 of the silicon wafer 42 with electrical interconnect 56 formed to electrically connect the photosensor array 28 and the readout electronics 30 using the conductive vias 43. The order of the fabrication steps of the photosensor array 28 and the readout electronics 30 may be changed and the fabrications may be provided using any suitable method and/or as described in more detail herein. The silicon wafer 42 with integrated photosensor array 28 and readout electronics 30 forms a multilayer structure in some embodiments, which may be, for example, a two or three layer structure as described herein. However, a single layer structure also may be provided.

The silicon wafer 42 with integrated photosensor array 28 and readout electronics 30 is then formed into 2D tileable silicon chips at 108, such as through any suitable wafer dicing process. Thereafter the tileable silicon chips may be packaged to form a detector module, such as CT detector module that provides digital inputs/outputs and power supply inputs from the tileable silicon chips.

Figure 8:
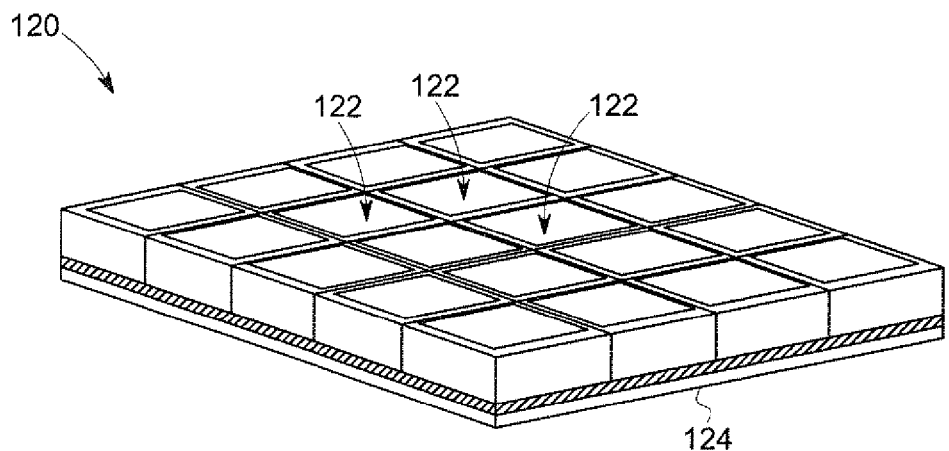
FIG. 8 is a perspective view of a detector module formed in accordance with an embodiment.

For example, as shown in FIG. 8, a plurality of sensor tiles 122 provided in accordance with various embodiments may form a detector module 120. The sensor tiles 122 may include a post-patient collimator, scintillator and the silicon chips with integrated photosensor arrays and readout electronics. For example, the detector module 120 may be configured as a CT detector module that includes a plurality, for example, twenty sensor tiles 122 arranged to form a rectangular array of five rows of four sensor tiles 122. The sensor tiles 122 are shown mounted on a printed circuit board 124 that may be coupled to processing and/or communication circuitry of a CT system. It should be noted that detector modules 120 having larger or smaller arrays of sensor tiles 122 may be provided. In operation, the x-ray signal detected by the sensor tiles 122 is generally determined from an integration of the total signal charges produced during a pre-defined period of time. However, other forms of signal sampling (e.g., readout of the signal corresponding to each individual x-ray) may be provided.

Figure 9:
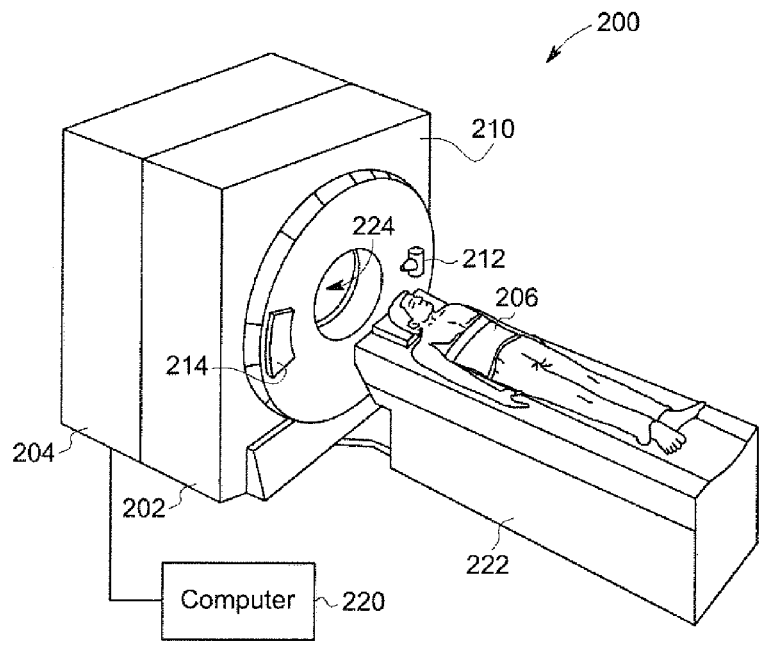
FIG. 9 is a pictorial drawing of an exemplary embodiment of an imaging system in which a detector module of various embodiments may be implemented.
Figure 10:
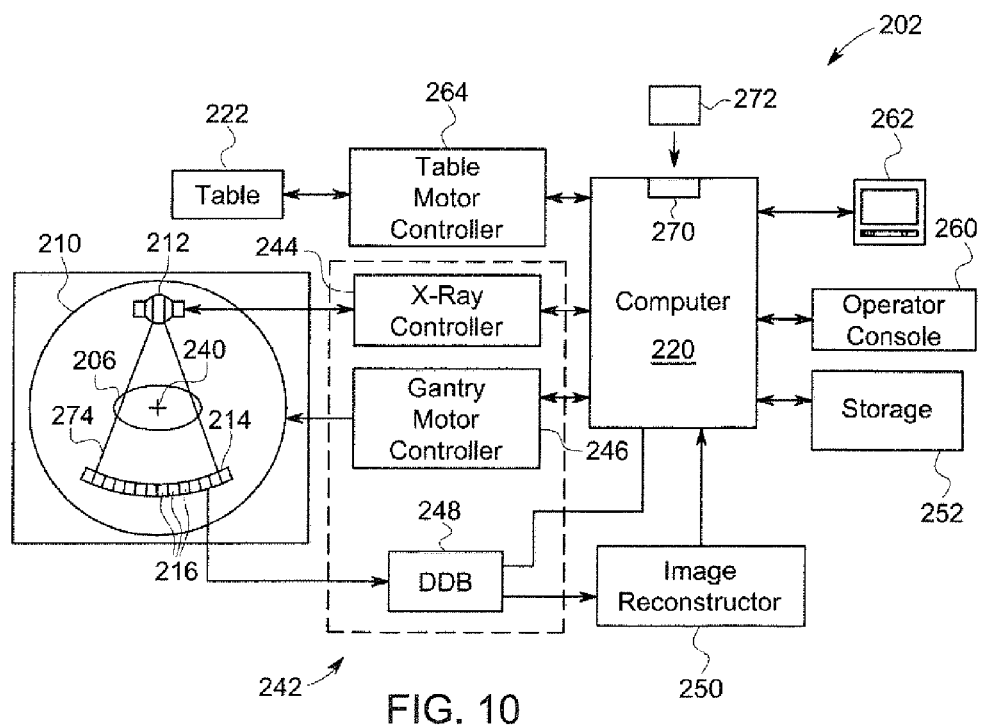
FIG. 10 is a schematic block diagram of the imaging system shown in FIG. 9.

The various embodiments may be implemented in connection with different types of imaging systems. For example, FIG. 9 is a pictorial view of an exemplary multi-modality imaging system 200 that is formed in accordance with various embodiments. FIG. 10 is a block schematic diagram of a portion of the imaging system 200 shown in FIG. 9. Although various embodiments are described in the context of an exemplary dual modality imaging system that includes a computed tomography (CT) imaging system and a positron emission tomography (PET) imaging system, it should be understood that other imaging systems capable of performing the functions described herein are contemplated as being used, including single modality imaging systems.

The multi-modality imaging system 200 is illustrated, and includes a CT imaging system 202 and a PET imaging system 204. The multi-modality imaging system 200 allows for multiple scans in different modalities to facilitate an increased diagnostic capability over single modality systems. In one embodiment, the exemplary multi-modality imaging system 200 is a CT/PET imaging system 200. Optionally, modalities other than CT and PET are employed with the multi-modality imaging system 200. For example, the imaging system 200 may be a standalone CT imaging system, a standalone PET imaging system, a magnetic resonance imaging (MRI) system, an ultrasound imaging system, an x-ray imaging system, and/or a single photon emission computed tomography (SPECT) imaging system, interventional C-Arm tomography, CT systems for a dedicated purpose such as extremity or breast scanning, and combinations thereof, among others.

The CT imaging system 202 includes a rotation gantry 210 that has an x-ray source 212 that projects a beam of x-rays 274 toward a detector array 214 on the opposite side of the rotation gantry 210. The detector array 214 includes a plurality of detector elements 216 that are arranged in rows and channels that together sense the projected x-rays that pass through an object, such as the subject 206, and which may be configured as multiple detector modules according to one or more embodiments described herein. The multi-modality imaging system 200 also includes a computer 220 that receives the projection data from the detector array 214 and processes the projection data to reconstruct an image of the subject 206. In operation, operator supplied commands and parameters are used by the computer 220 to provide control signals and information to reposition a motorized table 222. More specifically, the motorized table 222 is utilized to move the subject 206 into and out of the rotation gantry 210. Particularly, the motorized table 222 moves at least a portion of the subject 206 through a gantry opening 224 that extends through the rotation gantry 210.

As discussed above, the detector array 214 includes a plurality of detector elements 216. Each detector element 216 produces an electrical signal, or output, that represents the intensity of an impinging x-ray beam 274 and hence allows estimation of the attenuation of the beam as it passes through the subject 206. During a scan to acquire the x-ray projection data, the rotation gantry 210 and the components mounted thereon rotate about a center of rotation 240. The multi-slice detector array 214 includes a plurality of parallel detector rows of detector elements 216 such that projection data corresponding to a plurality of slices can be acquired simultaneously during a scan.

Rotation of the rotation gantry 210 and the operation of the x-ray source 212 are governed by a control mechanism 242. The control mechanism 242 includes an x-ray controller 244 that provides power and timing signals to the x-ray source 212 and a gantry motor controller 246 that controls the rotational speed and position of the rotation gantry 210. A digital data buffer (DDB) 248 in the control mechanism 242 receives and store the digital data from the detector array 214 for subsequent process. An image reconstructor 250 receives the sampled and digitized x-ray data from the DDB 248 and performs high-speed image reconstruction. The reconstructed images are input to the computer 220 that stores the image in a storage device 252. Optionally, the computer 220 may receive the sampled and digitized x-ray data from the DDB 248. The computer 220 also receives commands and scanning parameters from an operator via a console 260 that has a keyboard. An associated visual display unit 262 allows the operator to observe the reconstructed image and other data from computer.

The operator supplied commands and parameters are used by the computer 220 to provide control signals and information to the DDB 248, the x-ray controller 244 and the gantry motor controller 246. In addition, the computer 220 operates a table motor controller 264 that controls the motorized table 222 to position the subject 206 in the rotation gantry 210. Particularly, the motorized table 222 moves at least a portion of the subject 206 through the gantry opening 224 as shown in FIGS. 9 and 10.

Referring again to FIG. 10, in one embodiment, the computer 220 includes a device 270, for example, a floppy disk drive, CD-ROM drive, DVD drive, magnetic optical disk (MOD) device, or any other digital device including a network connecting device such as an Ethernet device for reading instructions and/or data from a computer-readable medium 272, such as a floppy disk, a CD-ROM, a DVD or an other digital source such as a network or the Internet, as well as yet to be developed digital means. In another embodiment, the computer 220 executes instructions stored in firmware (not shown). The computer 220 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the x-ray source 212 and the detector array 214 are rotated with the rotation gantry 210 within the imaging plane and around the subject 206 to be imaged such that the angle at which an x-ray beam 274 intersects the subject 206 constantly changes. A group of x-ray attenuation measurements, i.e., projection data, from the detector array 214 at one gantry angle is referred to as a "view". A "scan" of the subject 206 comprises a set of views made at different gantry angles, or view angles, during one revolution of the x-ray source 212 and the detector array 214. In a CT scan, the projection data is processed to reconstruct an image that corresponds to a two dimensional slice taken through the subject 206.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, Reduced Instruction Set Computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A detector comprising:
    a silicon wafer formed from a first layer having a first resistivity and a second layer having a second resistivity, wherein the first resistivity is greater than the second resistivity;
    a photosensor device provided with the first layer on a first side of the silicon wafer; and
    one or more readout electronics provided with the second layer on a second side of the silicon wafer, the first side being a different side than the second side.

2. The detector of claim 1, wherein the first side is opposite the second side.

3. The detector of claim 1, further comprising one or more conductive vias through the silicon wafer interconnecting the photosensor device and the one or more readout electronics.

4. The detector of claim 1, wherein the photosensor device comprises a photosensor array having a plurality of photodiodes that are fabricated in the first layer, and the one or more readout electronics comprise a plurality of readout electronics that comprise a plurality of analog to digital converters that are fabricated in the second layer.

5. The detector of claim 1, further comprising interconnect bonds on a surface of the second layer.

6. The detector of claim 5, wherein the interconnect bonds interconnect the one or more readout electronics with a controller of an imaging system, the interconnect bonds providing communication of at least one of digital signals or power signals.

7. The detector of claim 1, further comprising a third layer between the first and second layers, wherein the third layer has a lower resistivity than the first layer and the second layer.

8. The detector of claim 1, further comprising an isolation structure formed in the first layer and extending into the second layer.

9. The detector of claim 8, wherein the isolation structure is formed between the photosensor device and a conductive via.

10. The detector of claim 1, further comprising one or more conductive vias through the silicon wafer interconnecting the photosensor device and the one or more readout electronics and, further comprising electrical connectors connecting the one or more conductive vias with a doped region of the first layer.

11. The detector of claim 1, wherein the silicon wafer comprises a double sided epi-wafer.

12. An imaging system comprising:
    an x-ray source for generating x-rays;
    a detector for detecting x-rays generated by the x-ray source after passing through an object, the detector comprising a plurality of modules having detector elements formed from (i) a silicon wafer having a first layer with a first resistivity and a second layer having a second resistivity, wherein the first resistivity is greater than the second resistivity, (ii) a photosensor device provided with the first layer on a first side of the silicon wafer and (iii) one or more readout electronics provided with the second layer on a second side of the silicon wafer, the first side being a different side than the second side, wherein digital signals are output from the detector elements; and
    a processor for reconstructing an image of the object using the digital signals.

13. The imaging system of claim 12, wherein the detector elements further comprise tileable detector elements.

14. The imaging system of claim 12, wherein the detector elements further comprise one or more conductive vias through the silicon wafer interconnecting the photosensor device and the one or more readout electronics.

15. The imaging system of claim 12, wherein the photosensor device comprises a photosensor array having a plurality of photodiodes that are fabricated in the first layer, and the one or more readout electronics comprise a plurality of readout electronics that comprise a plurality of analog to digital converters that are fabricated in the second layer.

16. The imaging system of claim 12, further comprising a controller, wherein the detector elements further comprise interconnect bonds on a surface of the second layer interconnecting the one or more readout electronics with the controller, the interconnect bonds providing communication of at least one of digital signals and power signals.

17. The imaging system of claim 12, wherein the detector elements further comprise a third layer between the first and second layers, wherein the third layer has a lower resistivity than the first layer and the second layer.

18. The imaging system of claim 12, wherein the detector elements further comprise an isolation structure formed in the first layer and extending into the second layer.

19. A method for forming a detector module, the method comprising:
    fabricating a photosensor array on a first side of a silicon wafer, wherein the silicon wafer comprises a plurality of layers each having a different resistivity;
    fabricating readout electronics on a second side of the silicon wafer opposite the first side; and
    forming a conductive via through the silicon wafer interconnecting the photosensor array and the readout electronics.

20. The method of claim 19, further comprising forming an isolation structure on the first side of the silicon wafer to electrically isolate a photosensor pixel from adjacent photosensor pixels.

* * * * *